United States Patent [19]

Richter

[11] 4,207,881
[45] Jun. 17, 1980

[54] HEADGEAR FOR SUPPORT OF BROKEN JAWS DURING HEALING

[76] Inventor: Alice E. Richter, 260 N. Cache, P.O. Box 1901, Jackson, Wyo. 83001

[21] Appl. No.: 854,098

[22] Filed: Nov. 23, 1977

[51] Int. Cl.² ............................................. A61F 5/04
[52] U.S. Cl. .................................. 128/89 A; 128/163
[58] Field of Search ................ 128/76 R, 76 B, 89 R, 128/89 A, 163, 87 R

[56] References Cited

U.S. PATENT DOCUMENTS

| | | | |
|---|---|---|---|
| 2,151,458 | 3/1939 | Allen | 128/89 A |
| 2,325,300 | 7/1943 | Bisnoff | 128/89 A |
| 2,397,648 | 4/1946 | Butler | 128/89 A |
| 2,507,617 | 5/1950 | Swendiman | 128/89 A |
| 2,571,461 | 10/1951 | Livingston et al. | 128/89 A |
| 3,741,202 | 6/1973 | Morgan | 128/76 B |
| 3,759,256 | 9/1973 | O'Malley | 128/89 A |

*Primary Examiner*—John D. Yasko
*Attorney, Agent, or Firm*—James J. Conlon

[57] ABSTRACT

A comfortable headgear is worn by persons having broken jaws or other facial bones that must be held in place to set. The headgear can also be used in the treatment of bone spurs without the use of surgery. An adjustable headband circles the wearer's head and provides for attachment of intersecting skull straps that crisscross and snugly fit atop the wearer's head. The wearer's chin and lower jaw are engaged by a depending supporting portion that includes downwardly extending temple straps that are adjustably attached and movable along the headband portion and also adjustable in length to thereby provide a completely customized and comfortable fit. The temple straps intersect in a chin pad that has an X-shape with different length portions that may be located in such a fashion to customize the chin pad to the particular wearer and position the temple straps away from the wearer's cheeks to prevent irritation.

3 Claims, 3 Drawing Figures

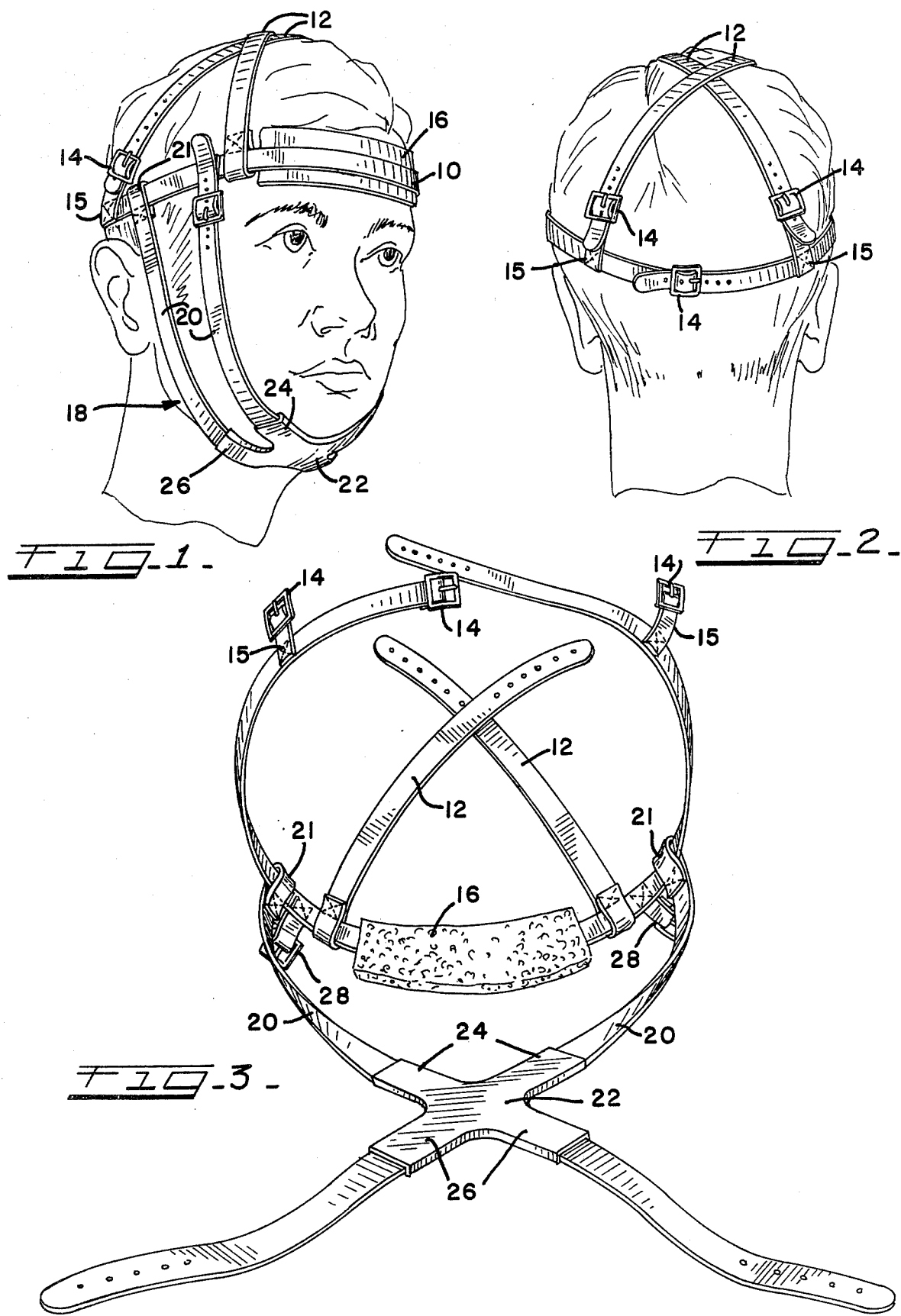

HEADGEAR FOR SUPPORT OF BROKEN JAWS DURING HEALING

BACKGROUND OF THE INVENTION (1) Field of the Invention

This invention pertains to supports used in setting broken jaws or treating bone spurs that include members attached about the skull portion of a wearer.

(2) Description of the Prior Art

Prior art devices such as the *Swendiman*, U.S. Pat. No. 2,507,617 (1950) and the *Preston*, U.S. Pat. No. 1,992,904 (1935) provide headgear units that have a strap type head supporting unit with a molded or solid chin support. The chin engaging portions are rigid and therefore almost impossible to fit properly to conform to the contour of the person's chin and lower jaw. Furthermore, the chin strap units are hot and uncomforable to wear eventhough attempts have been made as shown in the *Preston* illustrations to ventilate the chin supporting member. Other problems with rigid chin support, in addition to the difficulty in customizing each chin support to fit the wearer's bone contour, arise because of heat problems and unsanitary conditions which could occur in the absence of proper cleaning and maintenance. Furthermore, these chin supports engage the frontal chin portion of the wearer and have little or minimal force application to the underside of the wearer's jaw where jaw holding forces should be applied.

SUMMARY OF THE INVENTION

This invention pertains to a lightweight, flexible headgear for use by persons having broken jaws or bone spurs in the tempro-mandibular joint. An adjustable headband is fitted about a wearer's head and snugly held in place through the use of adjustable skull straps that extend from each side atop the wearer's head to the other side and are adjustable in length. Extending downwardly from the front portion of the headband are a pair of chin supporting temple straps that are attached to the headband in such a fashion as to be movable along the side of the headband and thus can be positioned at a point that provides maximum comfort and force application for healing of the broken jaw. These temple strap members crisscross underneath the wearer's lower jaw and pass through a chin pad that contacts the wearer's lower jaw. The end portions of each temple strap contains adjustment means to allow the strap to be tightened until a comfortable yet effective fit is effected.

The chin pad of this invention is shaped to fit on the underside of the lower jaw and includes portions that extend to the sides of the jaw in such fashion to keep the supporting temple straps away from the wearer's face. Thus, tightening forces carried by the temple straps, which hold the jaw bones together during healing, make the temple straps taut; however, the straps come in minimal contact with the person's cheeks thereby eliminating irritation.

If the wearer desires, the headgear may be removed for shaving by men or to take a shower, put on makeup or the like.

The headgear has no cumbersome portions extending from the wearer's face and thus the headgear may be worn during sleeping without inconvenience.

These and other features and advantages of the invention will become apparent to those skilled in the art from the following description, attached drawings and appended claims.

BRIEF DESCRIPTION OF THE DRAWINGS

FIG. 1 is a view showing details of the frontal portion and chin pad of the headgear;

FIG. 2 is a rear pictorial illustration of the headgear in place on the wearer; and FIG. 3 is a rear illustration of the headgear removed from the wearer.

DETAILED DESCRIPTION

When a broken jaw occurs it is first necessary to manually align the broken sections and wire together the person's upper and lower teeth to hold the bones in a position normally assumed by the bones. However, the lower jaw, the mandible, must be supported or its weight will cause the broken sections to be pulled downwardly and improper setting of the broken jaw will occur. Thus, it is necessary to support the lower jaw during healing of some maxillary and mandibular fractures.

Referring now to the drawings and in particular to FIG. 1, a headgear unit is shown as worn by a person having a broken jaw or having bone spurs at the tempro-mandibular joint. A headband 10 is located about the person's cranium or skull. Skull straps 12, including end portions fixedly attached to the front part of the headband, are crisscrossed about the wearer's head and, like the headband 10 include buckles or other adjustment means 14 for varying the length to provide a customized fit about the wearer's head. Thus, the head engaging portion of the headgear provides a unit that may be customized or fit to the particular head shape or hair style or other dimension of the wearer's head. This is particularly important where injuries other than a broken jaw have been inflicted on a person's head and there may be scarring, open wounds or bandages that must be avoided by the headgear supporting straps. To provide for customized fitting, each of the skull straps 12 includes an end portion 15 that is looped about the headband 10 in such a fashion as to permit the straps to be positioned or located at various points along the headband 10.

It is recommended that the headgear and skull straps be constructed of leather or another material that does not easily stretch and can be firmly held in place after tightening. It is also recommended that the headband have a length of at least 26 inches (66 cm.) and that each skull strap be at least 15 inches (38 cm.) in length. These members are to be sized rather long and contain many perforations if buckles are used for adjustment in order that the excess strap may be easily cut off after the headgear has been customized and properly fit to the particular wearer's head dimensions.

The front portion of the headband includes a sheepskin 16 for preventing direct contact between the wearer's forehead and the headband strap 10. The sheepskin is desirable because it is compatable with tissue and used in hospitals to eliminate bed sores.

A frontal chin strap unit 18 is positioned at the front portion of the headband 10 and includes a pair of front and rear temple straps 20 depending therefrom and extending downwardly alongside the wearer's face but not in tight contact with the face. Each temple strap 20 includes a loop portion 21 for attaching the temple strap 20 to the headband 10 in such a fashion that the temple strap 20 can be located at various positions along the headband 10. A jaw support pad 22 receives an intermediate portion of each temple strap 20 and allows the temple straps 20 to crisscross. It is noticed in FIG. 3, the jaw support pad 22 provides a somewhat X-shaped member having two shorter leg members 24 and two longer leg members 26. These different length legs are provided in order that the jaw support pad may accommodate persons having various jaw and chin dimensions and geometries. For example, the person with somewhat of a pointed chin could have a shorter leg portion 24 located in the chin area. On the other hand, a person with a broader chin could require the longer leg members 26 to be placed forward and underneath the wearer's chin.

The end portions of the temple straps 20 are thereafter connected to the front attachment or buckle 28 which are positioned about the headband 10. It is contemplated that the front attachments 28 may also be adjustable attached about the headband and thereby located at various positions on the headband to customize the chin strap location to the particular wearer.

The temple straps are contemplated as being approximately 20 inches (50 cm.) in length. Like the other straps, excess length can be cut off after the headgear is fitted on the wearer.

In operation, when the headgear is attached to a person for setting a maxilla or mandible that has been broken, it is first positioned about the top portion of the wearer's head or skull beginning with the headband 10 being comfortably yet firmly tightened about the skull. Thereafter, the skull straps 12 are tightened into position to provide a unit with the headband that is firmly attached about the wearer's head. Next, the frontal chin strap unit 18 is comfortably positioned beginning with locating chin support pad 22 at a comfortable and effective position below the wearer's lower jaw. Thereafter temple straps 20 are located at a point in front of or behind the wearer's ear as may be determined by the jaw structure and head geometry of the wearer. After the temple strap 20 and jaw support pad 22 have been comfortably located, the end portions of the temple straps 20 are tightened into their respective front attachment buckles 28 and tightened to produce an effective unit for holding and urging the lower jaw upward for healing.

It is noticed that the jaw support pad 22 extends to the outside of the wearer's lower jaw in such a fashion as to allow the temple straps 20 to extend alongside the person's face in minimal or no contact with the face. Thus, tightening forces that extend from the headband to the jaw support strap will cause little contact between the temple straps 20 and the wearer's face thus eliminating any irritation that could occur.

It is noticed that once the headgear has been positioned on the wearer there are no rigid parts in contact with the person nor are there any parts extending from the headgear that could become entangled while the wearer is sleeping. Further, the headgear may be loosened or removed for bathing, shaving or applying makeup and later easily refitted by the wearer.

The foregoing description and drawings merely explain and illustrate the invention and the invention is not limited thereto, except insofar as the appended claims are so limited, as those who are skilled in the art and have the disclosure before them will be able to make modifications and variations therein without departing from the scope of the invention.

What is claimed is:

1. A removable headgear for attachment about the head of a person and for supporting the person's lower jaw for use in assisting in treatment of bone spurs and setting of broken jaws or other facial bones, the improvement comprising:
    a headband for fitting about the wearer's head;
    adjustment means for varying the circumference of the headband;
    skull support means extending across the headband;
    means depending from the headband and including strap means extending downwardly for support of the lower jaw of the wearer;
    said means depending from the headband also including adjustable ends attachable with cooperative means mounted on the headband for varying the length of the depending means to provide a comfortable snug attachment for supporting and engaging the wearer's face;
    a chin pad;
    said chin pad having means extending outwardly of the wearer to position said strap means in a non-irritating position on the wearer;
    a first strap;
    a second strap;
    said chin pad having intersecting means to criss-cross said first and second straps for supporting the lower jaw;
    said intersecting means having adjustable means for sliding the first and second straps to adjust the location of the chin strap and to allow for removal of the intersecting means.

2. The headgear of claim 1 wherein said skull support means includes:
    first and second skull bands;
    each skull band having means for movably attaching the skull bands to said headband for positioning said skull bands at various points along the headband to customize the fit of the headgear.

3. The headgear of claim 1 wherein said skull support means includes:
    position adjustment means for locating one end of said skull support means at various positions on said headband;
    means for adjusting the length of said skull support means to customize the fit of said headgear for the wearer.

* * * * *